US00PP23509P2

(12) United States Plant Patent
Hanes

(10) Patent No.: US PP23,509 P2
(45) Date of Patent: Apr. 2, 2013

(54) ***PELARGONIUM* PLANT NAMED 'PECZ0003'**

(50) Latin Name: *Pelargonium×hortorum*
Varietal Denomination: PECZ0003

(75) Inventor: Mitchell E. Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 2 days.

(21) Appl. No.: 13/317,385

(22) Filed: Oct. 17, 2011

(51) Int. Cl.
*A01H 5/00* (2006.01)

(52) U.S. Cl. ..... Plt./325; Plt./324

(58) Field of Classification Search ..... Plt./324, Plt./325

See application file for complete search history.

*Primary Examiner* — Susan McCormick Ewoldt

(74) *Attorney, Agent, or Firm* — Joshua L. Price

(57) ABSTRACT

A new *Pelargonium* plant named 'PECZ0003' particularly distinguished by the large inflorescences borne well above the foliage, bi-colored white to light pink flowers with large red-purple blotches, medium green foliage without zonation, with mounded, well-branched plant habit.

1 Drawing Sheet

Latin name of the genus and species of the plant claimed: *Pelargonium×hortorum.*

Varietal denomination: 'PECZ0003'.

BACKGROUND OF THE NEW PLANT

The present invention comprises a new zonal Geranium, botanically known as *Pelargonium×hortorum* and hereinafter referred to by the variety name 'PECZ0003'.

'PECZ0003' is a product of a planned breeding program. The new cultivar has large inflorescences borne well above the foliage, bi-colored white to light pink flowers with large red-purple blotches, medium green foliage without zonation, with mounded, well-branched plant habit.

'PECZ0003' originated from a hybridization made in January 2007 in a controlled breeding program in Gilroy, Calif., USA. The female parent was the proprietary, unpatented plant designated '10286-14' with single type, white splash colored flowers and with relatively light green foliage. The male parent was also a proprietary, unpatented plant designated as '10282-1' with a single type, light pink with splash colored flowers and lighter green foliage.

The resulting seeds were sown in May 2007 and 'PECZ0003' was selected as one flowering plant within the progeny of the stated cross in September 2007 in a controlled environment in Gilroy, Calif.

The first act of asexual reproduction of 'PECZ0003' was accomplished when vegetative cuttings were propagated from the initial selection in September 2007 in Gilroy, Calif. USA.

BRIEF SUMMARY OF INVENTION

Horticultural examination of plants grown from cuttings of the plant initiated in the September 2007 in Gilroy, Calif., and continuing thereafter, has demonstrated that the combination of characteristics as herein disclosed for 'PECZ0003' are firmly fixed and are retained through successive generations of asexual reproduction.

'PECZ0003' has not been observed under all possible environmental conditions. The phenotype may vary significantly with variations in environment such as temperature, light intensity and day length.

Plant Breeder's Rights for this cultivar were applied for in Switzerland on Dec. 16, 2010, #10-2699, in Canada on Dec. 17, 2010, #10-7129 and in the EU Community Plant Variety Office (CPVO) on Jan. 6, 2011, #2011/0066. 'PECZ0003' has not been made publicly available more than one year prior to the filing of this application.

The following traits have been repeatedly observed and are determined to be basic characteristics of the new variety. The combination of these characteristics distinguishes this *Pelargonium* as a new and distinct variety.

BRIEF DESCRIPTION OF THE PHOTOGRAPH(S)

The accompanying photographic drawing shows typical flower and foliage characteristics of 'PECZ0003' with colors being as true as possible with an illustration of this type. The photographic drawing shows a flowering potted plant and a close view of a flower of the new variety.

DETAILED BOTANICAL DESCRIPTION

The plant used for the photographs were about 10-11 weeks old, grown in Gilroy, Calif. USA, in a greenhouse trial. The photograph was taken in the end of March, 2011.

The plant descriptions and measurements were taken in Hillscheid, Germany in May 2010 on 11 week old plants that were growing in a greenhouse. Cultivation of these plants had started in mid February 2010 when rooted cuttings were planted into 12 cm pots and grown without pinching, at a minimum day temperature of 16° C. until April 1, and cool morning culture for keeping plants compact. After April 1, temperature was generally higher.

Color references are made to The Royal Horticultural Society Colour Chart (R.H.S.) 2001.

TABLE 1

DIFFERENCES BETWEEN THE NEW VARIETY 'PECZ0003' AND A SIMILAR VARIETY

| | 'PECZ0003' | 'Amri Whits09' (U.S. Plant Pat. No. 20,378) |
|---|---|---|
| Flower color: | White to sometimes pale pink | Less pink and more white |
| Flower diameter: | Wider | Narrower |
| Flower quantity: | More | Less |
| Branch length: | Shorter | Longer |
| Plant habit width: | Narrower in summer | Wider in summer |

Plant:

*Form, growth and habit.*—Bushy, well-branched and rounded habit, about medium vigor.

*Plant height.*—13.7 cm.

*Plant height (inflorescence included).*—23.5 cm.

*Plant width.*—26.2 cm.

Roots:

*Number of days to initiate roots.*—About 15 days at about 22 degrees C.

*Number of days to produce a rooted cutting.*—21-24 days at 22 degrees C.

*Type.*—Fine, fibrous, free branching.

*Color.*—RHS N155B.

Foliage:

*Immature leaf, color of upper surface.*—RHS 137C to 137D.

*Immature leaf, color of lower surface.*—RHS 138B.

*Mature leaf, color, upper surface.*—RHS 137B, RHS137C or RHS137D.

*Mature leaf, color of lower surface.*—Between RHS 138A and RHS138B.

*Length.*—5.0-6.0 cm.

*Width.*—8.0-10.0 cm.

*Shape.*—Reniform, with moderate lobes, slightly wavy margins and palmate venation.

*Base shape.*—Cordate, with open to wide open gap between the lowest lobes.

*Apex shape.*—Rounded.

*Margin.*—Bi-crenate.

*Foliage fragrance.*—Slight aroma typical for zonal geraniums.

*Texture.*—Velvety upper, both surfaces pubescent.

*Color of zone.*—Absent.

*Color of veins, upper surface.*—RHS 144A, hardly visible.

*Color of veins, lower surface.*—RHS 144B or RHS145A.

*Petiole, color.*—RHS 143B to RHS143C.

*Petiole, length.*—7.0-9.0 cm.

*Petiole diameter.*—0.3 cm.

*Texture.*—Densely covered with short hair, some glandular hairs.

Stem:

*Number of branches.*—6 to 10; 7.8 on average.

*Color of stem.*—RHS 143B to RHS143C, no anthocyanin.

*Length of stem.*—9.0-12.0 cm.

*Diameter.*—0.6-0.7 cm.

*Length of internodes.*—1.0-1.5 cm.

*Texture.*—Densely covered with short, glandular hair.

Peduncle:

*Color.*—RHS 143B to 143C.

*Length.*—About 15.8 cm.

*Diameter.*—About 0.4 cm.

*Texture.*—Dense glandular hair, and a few soft, longer hairs.

Pedicel:

*Color.*—RHS 143B to RHS143C, RHS 146B at the upper end.

*Length.*—4.3 cm.

*Diameter.*—1.5-2.0 mm.

*Texture.*—Dense, short glandular hair.

Inflorescence:

*Type.*—An umbel, semi-spherical or nearly semi-spherical, tight, medium sized.

*Blooming habit.*—Beginning of flowering with 50% of plants with open flowers: About mid-April, on about 9-week-old plants.

*Lastingness of individual flowers.*—7-9 days at 18° C. temperature.

*Number of inflorescences per plant.*—2-3.

*Number of flowers and buds per inflorescence.*—About 20 to 25.

*Umbel diameter.*—About 13.1 cm.

*Umbel depth.*—6.0-7.0 cm.

*Fragrance.*—None.

Bud (just before opening):

*Color.*—About RHS 49D.

*Length.*—1.8-2.4 cm.

*Width.*—0.9-1.4 cm.

*Shape.*—Elliptical.

Corolla:

*Form and shape.*—Single, shallow funnel-shape.

*Flower diameter.*—About 5.1 cm.

*Depth of flower.*—Approx. 1.7-2.1 cm.

*Number of petals.*—5.

Upper petals:

*Color upper surface.*—RHS 155B or sometimes RHS 69D with large blotches of RHS N57A to RHS N66B, a small white base, and with RHS 67B veins.

*Color lower surface.*—Closest to RHS 69D; with RHS N66C veins.

*Length.*—2.8-3.2 cm.

*Width.*—2.7-2.9 cm.

Lower petals:

*Color upper surface.*—RHS N155B to RHS 69D with medium to large macules, more red than RHS N57A.

*Color lower surface.*—Between RHS N155B and 65D.

*Length.*—2.7-2.9 cm.

*Width.*—2.6-2.9 cm.

*Petal shape.*—Obovate.

*Apex shape.*—Rounded.

*Margin.*—Entire.

*Petal texture.*—Glabrous.

*Number of petaloids.*—None.

Calyx:

*Number of sepals.*—5, occasionally 6, in a whorl, fused at the base.

*Color of sepals, abaxial surface.*—RHS 143B.

*Color, adaxial (inner) surface.*—RHS 143C.

*Length of sepals.*—1.2-1.4 cm.

*Width of sepals.*—0.3-0.5 cm.

*Sepal shape.*—Lanceolate.

*Apex shape.*—Acute.

*Margins.*—Entire.

*Texture outer surface.*—Short glandular hair; a few longer, soft hairs at the base.

*Texture inner surface.*—Smooth, glabrous.

Reproductive organs:

*Pistil.*—1.

*Length.*—0.9-1.1 cm.

*Style color.*—RHS N57D to RHS63C.

*Style length.*—0.4-0.5 cm.

*Stigma color.*—RHS 63D.

*Ovary color.*—RHS 138B.

*Ovary shape.*—Elongate.

*Ovary length.*—0.4-0.5 cm.

*Number of stamen.*—7 to 9.

*Length of anthers.*—0.2-0.3 cm.

*Anther color.*—RHS 47C.

*Length filaments.*—About 0.6 to 0.9 cm.

*Color of filaments.*—RHS 155A, occasionally with a little RHSN57D near upper end.

*Pollen amount.*—Moderate.

*Color of pollen.*—RHS N25A.

*Fertility/seed set.*—Not observed on this hybrid.

*Disease/pest resistance.*—Not observed on this hybrid.

What is claimed is:

1. A new and distinct variety of *Pelargonium* plant named 'PECZ0003' substantially as illustrated and described herein.

* * * * *

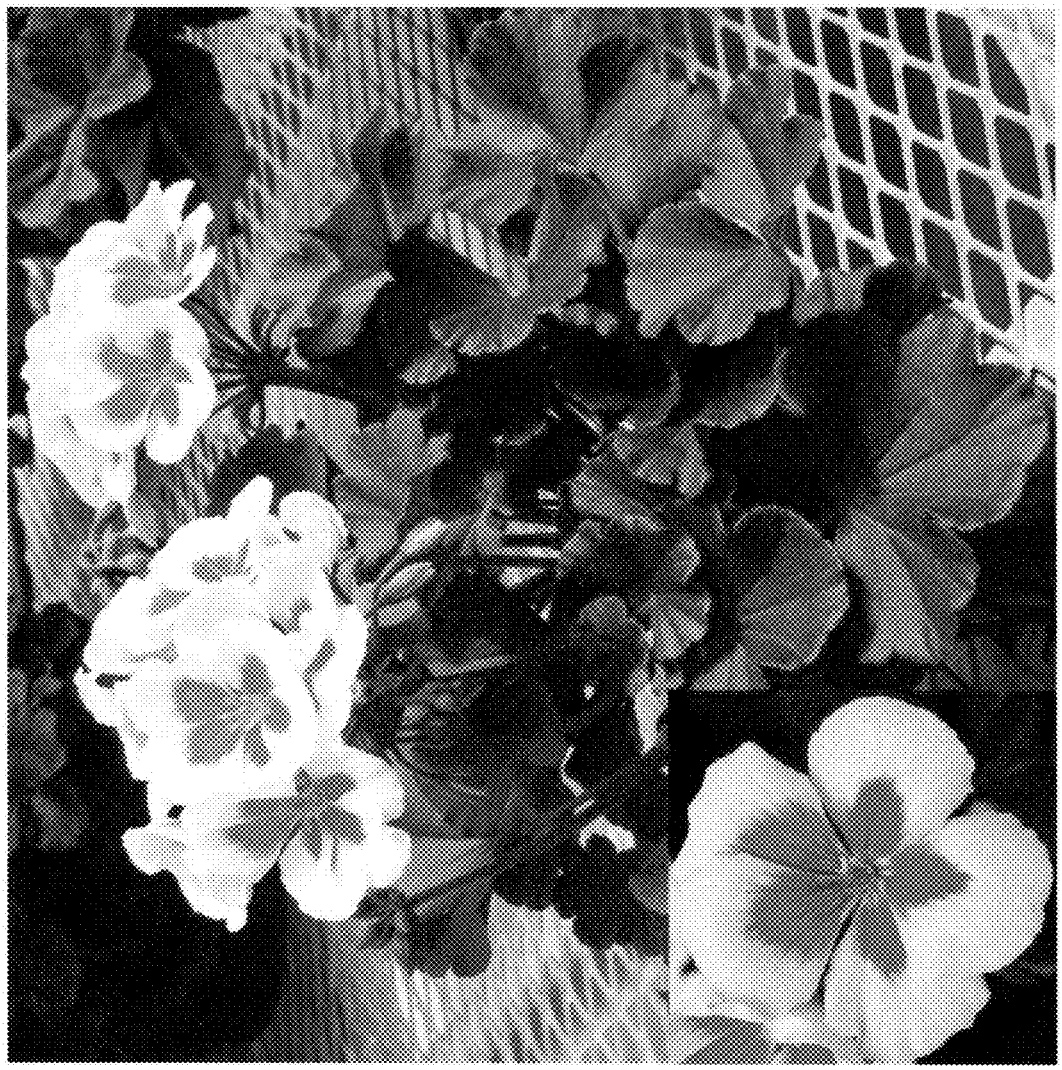

UNITED STATES PATENT AND TRADEMARK OFFICE

CERTIFICATE OF CORRECTION

PATENT NO. : PP23,509 P2
APPLICATION NO. : 13/317385
DATED : April 2, 2013
INVENTOR(S) : Hanes It is certified that error appears in the above-identified patent and that said Letters Patent is hereby corrected as shown below:

In the Specifications:

At column 1, line 38, delete "the" before --September 2007--

At column 3, line 32, delete "RHS137C or RHS137D" and insert therefor --RHS 137C or RHS 137D--

At column 3, line 34, delete "RHS138B" and insert therefor --RHS 138B--

At column 3, line 50, delete "RHS145A" and insert therefor --RHS 145A--

At column 3, line 51, delete "RHS143C" and insert therefor --RHS 143C--

At column 3, line 58, delete "RHS143C" and insert therefor --RHS 143C--

At column 4, line 5, delete "RHS143C" and insert therefor --RHS 143C--

At column 5, line 4, delete "RHS63C" and insert therefor --RHS 63C--

At column 6, line 3, delete "RHSN57D" and insert therefor --RHS N57D--

Signed and Sealed this
Fourteenth Day of May, 2013

Teresa Stanek Rea
*Acting Director of the United States Patent and Trademark Office*